United States Patent [19]
Delrieu et al.

[11] Patent Number: 5,962,015
[45] Date of Patent: Oct. 5, 1999

[54] STABILIZED LIPOSOMES

[75] Inventors: Pascal Delrieu; Li Ding, both of Castanet Tolosan, France

[73] Assignee: Kobo products s.a.r.l., France

[21] Appl. No.: 08/850,052

[22] Filed: May 2, 1997

[51] Int. Cl.⁶ .................................................. A61K 9/127
[52] U.S. Cl. ........................................... 424/450; 424/401
[58] Field of Search ..................................... 424/450, 401, 424/417; 935/54

[56] References Cited

U.S. PATENT DOCUMENTS

| | | | |
|---|---|---|---|
| 4,839,175 | 6/1989 | Guo | 424/450 |
| 5,244,672 | 9/1993 | Huc et al. | |
| 5,283,228 | 2/1994 | Narayanan et al. | |
| 5,393,527 | 2/1995 | Malick et al. | |
| 5,469,854 | 11/1995 | Unger et al. | |
| 5,498,420 | 3/1996 | Mentrup et al. | |
| 5,518,647 | 5/1996 | Zocchi | 252/174.17 |
| 5,531,925 | 7/1996 | Landh et al. | |
| 5,580,575 | 12/1996 | Unger et al. | |
| 5,597,549 | 1/1997 | Schneider et al. | |

FOREIGN PATENT DOCUMENTS 0162724  11/1985  European Pat. Off. .

OTHER PUBLICATIONS

Henriksen Internet. J. of Pharmaceuticals. 101 p. 227 1994.
Fiche Technique, "Pro–Lipos", Lucas Meyer France S.A.

*Primary Examiner*—Gollamudi S. Kishore
*Attorney, Agent, or Firm*—Handal and Morofsky

[57] ABSTRACT

Lecithin-type liposomes are stabilized with quaternized alkyated polymers, such as steardimonium hydroxyethylcellulose, to provide excellent stability for cosmetic and pharmaceutical formulations. Temperature, storage, solvent, and acidity stability are described. The stabilized liposomes can serve as vectors for alpha-hydroxy acids and showed no aggregation even after 4 months of storage at pH 2.

25 Claims, 1 Drawing Sheet

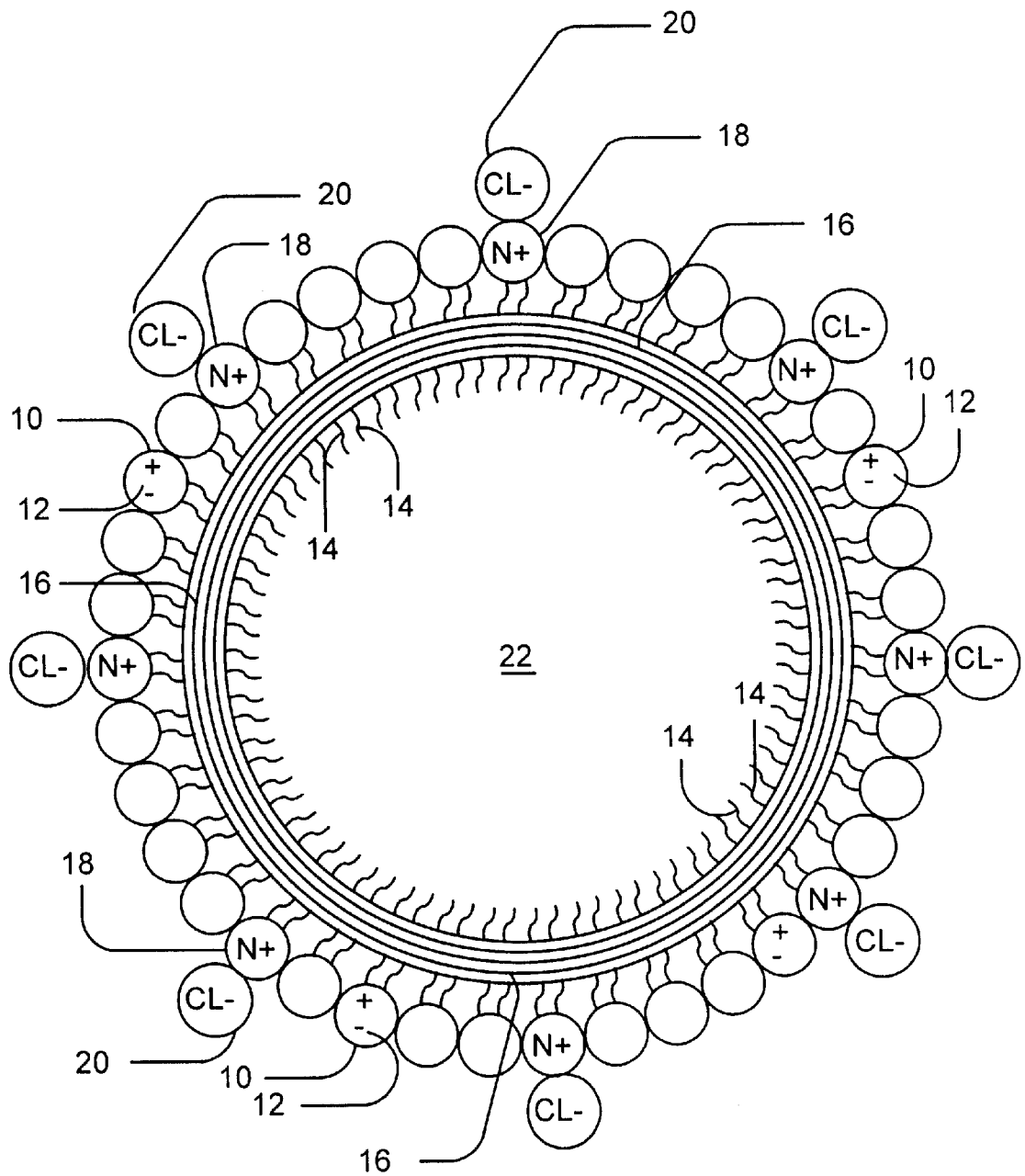

STABILIZED LIPOSOMES

BACKGROUND OF THE INVENTION

1. Field of the Invention

This invention relates to a stabilized liposome composition capable of conveying active agents in cosmetic or pharmaceutical compositions and delivering them to the skin or other biological target such as the nails, hair, mucous membranes or even internally. The liposomes are carriers for the actives and are sometimes described as vectors for their ability to transport the active agent. More particularly, in preferred embodiments, the invention provides stabilized liposome compositions which can encapsulate or other wise contain acidic, water-soluble active ingredients, for example AHA's in cosmetic compositions, especially emulsions, such as creams lotions and gels, adequately through formulation and storage to deliver the actives to consumers, patients, or others, with their activity retained.

Liposomes or "lipid bodies", sometimes called "vesicles" are structures formed spontaneously by polar lipid molecules, or amphiphilic molecules, each having a polar head and a long hydrophobic tail, e.g. phospholipids such as lecithin. Structurally, liposomes comprise an outer shell of one or more membrane-like, bilayers of the molecules arranged concentrically around a hollow interior, or "vacuole" which can serve as a storage compartment for active agents. In the outer layer the polar heads of the molecules are oriented outwardly of the liposome, while the hydrophobic tail, e.g. palmitic or stearic acid, depends inwardly. If there are multiple layers, the orientation is reversed in alternate layers so that the lipid tails of one layer intermingle with the lipid tails of the next, and the polar heads of one layer abut those of a neighbor.

Active agents may be stored in the interior of the liposome, where they are sheltered from alien media by the surrounding membrane of amphiphilic molecules. Such active agents may or may not be dissolved in aqueous media, and are typically hydrophilic. Typically also, the liposomes are dispersed in an aqueous medium, or polar solvent medium. Lipophilic active agents can also be carried by liposomes, locating themselves in the lipid layers formed by the hydrophobic tails of the amphiphilic structural liposome material. Gas filled liposomes are also known, see for example, Unger et al. U.S. Pat. Nos. 5,580,575, 5,469,854 which disclose the use of gas-filled liposomes for medical diagnostic purposes.

Liposomes are typically quite small, under 1 micron, and small enough to transport encapsulated actives through the dermis for sub-dermal delivery. For these and other reasons, liposomes are widely used in both the cosmetics and pharmacy industries in various applications for the delivery of cosmetically and pharmacologically active substances.

However, there are significant problems to be overcome in using liposomes for cosmetic or pharmaceutical formulations intended for consumer use. Known compositions lack sufficient stability to withstand formulating conditions and have a poor shelf life. Liposome vesicles tend to fuse together, or agglomerate, particularly when they are exposed to surfactants, solvents, adverse pH conditions, or even water, for long periods of time. This instability is usually aggravated by elevated temperatures or low pH levels, under which conditions the liposome vesicles may fuse together and aggregate into quasi-gellified suspensions of the component polar lipids.

Accordingly, there have been many proposals for stabilizing liposomes. Known stabilizers for liposomes include certain relatively simple amphoteric molecules having a cationic region, for example triethanolamine, a common cosmetic buffer, can be added to phospholipid starting materials during liposome preparation to prevent aggregation. Though providing some stability, triethanolamine and the like, do not provide adequate shelf-life and processing stability to enable liposomes to protect actives in a wide range of cosmetic and pharmaceutical formulations.

2. Description of Related Art Including Information Disclosed under 37 CFR 1.97 and 37 CFR 1.98

Huc et al. ("Huc") U.S. Pat. No. 5,244,672 discloses stabilization of liposomes with a support comprising non-crosslinked, "atelo" collagen and glycosaminoglycans. This support system is reported to provides a modest reduction of permeability of the liposome membrane to a fluorescent marker, designated "6-CF". No significant shelf life or temperature stability improvements are reported.

Edgar et al. U.S. Pat. No. 5,498,420 discloses liposome preparations comprising a mixture of lecithin and a fatty acid-esterified collagen hydrolysate, "namely a fatty acid ester of a lipoaminoacid or lipopeptide", see the Abstract. The liposomes produced reportedly show room temperature stability, column 21, and are incorporated into gels. However there is no data as to stability of the produced liposomes to elevated temperatures, surfactants, solvents other than water, or acidity.

Unger et al. ("Unger") U.S. Pat. No. 5,469,854 and 5,580,575 disclose gas-filled liposomes prepared by shaking at a temperature below the gel-to-crystalline phase transition temperature, using a process wherein the ingredients are frozen in liquid nitrogen. Unger's liposomes are intended, inter alia, as vehicles for lipophilic actives, and Unger teaches a range of possible stabilizers or viscosity modifiers, emulsifiers and solubilizers, see '575 col. 9, lines 11–39. Various possible coatings are also suggested, see col. 15, lines 2–10. Unger's liposomes are relatively large, with sizes in excess of 5 micron and typically in excess of 8 micron, see '854 col. 27. A principle application is for ultrasound diagnostics and delivery of actives to target sites for ultrasound-initiated release of actives.

Unger's catalogic lists provide no guidance as to the selection of a stabilizer for the purposes described herein. Nor does Unger appear to provide any teaching regarding liposome compositions suitable for protecting active agents in cosmetic and pharmaceutical compositions, during formulation and storage. There is accordingly a need for stabilized liposomes with such useful properties.

SUMMARY OF THE INVENTION

The invention, as claimed, is intended to provide a remedy. It helps solve the problem of liposome instability in cosmetic or pharmaceutical formulations.

Accordingly, the invention provides, in one aspect, a liposome dispersion stabilized with a stabilizing agent comprising a water soluble quaternized polysaccharide. In another aspect, the invention provides a stabilized liposome composition comprising:

a) an aqueous medium; and b) liposomes dispersed in the aqueous medium;

wherein the liposomes comprise sufficient water-soluble quaternized polysaccharide stabilizing agent to stabilize the liposomes against agglomeration.

Surprisingly it has been discovered that liposomes stabilized with a quaternized polysaccharide, for example a modified starch or cellulose, exhibit excellent and hithertofore unobtainable stability properties, and are stable to surfactants, solvents, or water, even when exposed to such materials for long periods of time, or to elevated temperatures, or both.

In some preferred embodiments, the quaternized polysaccharide comprises laurdimonium hydroxyethylcellulose, cocodimonium hydroxyethylcellulose or steardimonium hydroxyethylcellulose, the proportion of quaternized polysaccharide to liposomes is from about 0.01 to about 0.5 parts polysaccharide per part of liposome, by weight, wherein the liposomes comprise a liposome membrane-forming amphiphilic lecithin in a proportion of from about 0.5 to 10 percent by weight of the composition and wherein the individual liposomes contain an aqueous solution of an acidic cosmetically or biologically active ingredient.

The invention provides new possibilities for the delivery of actives to the skin surface. For example, the invention can be used to deliver alpha-hydroxy acids (AHAs) to the skin surface in a cosmetic formulation with a long shelf life. High concentrations of AHAs can be delivered with low irritation, or low risk of irritation, because the protective liposome membrane controls release of the AHA to the skin, limiting the degree to which the AHA penetrates to sensitive basal cells.

Data described hereinbelow show excellent stability results for liposomes prepared from highly purfied lecithin and a preferred quaternized, alkyl-substituted polymeric stabilizing agent, with regard to temperature, acidity and solvent tolerance. These findings are particularly noteworthy in view of the known difficulty of forming liposomes with purified lecithin and the instability of the resultant liposomes, which tend to aggregate rapidly.

The invention extends to a cosmetic or pharmaceutical composition comprising an effective amount of the inventive stabilized liposome composition, which liposome composition in turn comprises an effective amount of an active ingredient being labile when unprotected in the environment of the cosmetic or pharmaceutical composition, or during its formulation or manufacture.

BRIEF DESCRIPTION OF THE DRAWINGS

One or more ways of carrying out the invention are described in detail below with reference to the single FIGURE of the accompanying drawing which illustrates a single specific embodiment of the invention and is a schematic, much simplified cross-sectional view of a stabilized liposome according to the invention.

DETAILED DESCRIPTION OF THE PREFERRED EMBODIMENTS

All parts and proportions referenced in this description, unless otherwise stated, are on a weight or weight-for-weight basis.

In a preferred embodiment, the present invention provides stabilized liposomes by adding a quaternized cellulose to suitable liposome membrane-forming polar lipid material, notably lecithin, during formation of the liposomes, to inhibit the resultant liposomes from aggregating in the presence of solvents and surfactants or under adverse pH conditions. Referring to the drawing, a liposome particle, or vesicle, comprises a shell-like outer layer of lecithin molecules 10 arranged, in an idealized conception, on the surface of a sphere. The lecithin molecules have polar heads 12 aligned to the outside of the liposome particle, and each has twin hydrophobic, lipophilic fatty acid tails 14 shown as aligned generally radially inwardly. It may be surmised that the fatty acid tails 14, which bind weakly together, will intermingle with their neighbors lending lateral adhesion to the liposome structure. Equally, the polar character of the head 12 of a lecithin molecule has the nature of a dipole with a positive charge located in the vicinity of lecithin's distal quaternary nitrogen atom, and a negative charge in the vicinity of its neighboring phosphatidyl group. The structural formula may be depicted as follows:

wherein R is usually a medium chain alkyl group, such as linoleic, stearic, and the like. The dipoles can be expected to attract each other into side-by-side alignment in a staggered manner so that the positively charged nitrogen atom of one lecithin molecule 10 is adjacent the negatively charged phosphorus atoms of its immediate neighbors. These lateral attractions can be surmised as helping to hold the liposome together, but are pH sensitive.

A stabilizing polymer 16 is shown as a layer holding or embracing the hydrophobic tails 14 of the lecithin molecules 10, perhaps with its own pendant hydrophobic groups. This showing is certainly an oversimplification and it may be assumed that many of the polar heads 12 of the lecithin molecules will also be embraced by polymer 16. However, this depiction helps convey the notion that a molecule of polymer 16 may be of the order of 50–100 times the size of the structural membrane molecule 10. A small number of pendant quaternary nitrogens 18 are shown as interposed between the polar heads 12 of the lecithin molecules 10 where they attract chloride ions 20 (proportionately smaller than shown). The chloride ions 20 give the liposome an electronegative veil which repels other liposomes and deters agglomeration. The large polymer molecules help bind the liposome together, yet surprisingly, do not prevent its formation.

The liposome has an interior 22 which can harbor potent or labile active ingredients, safely contained within the lecithin-polymer shell.

The invention is in no way limited, or bound, by this model which may or may not be accurate, or appropriate, and is certainly, at best, a very rough approximation provided by way of explanation as to one possible mechanism of action leading to the excellent and surprising results obtained by the invention and to assist others in devising alternative ways to practice the invention.

Liposome membrane-forming materials. Phospholipids commonly used to synthesize liposomes include soybean lecithin, a by-product in the manufacturing of soybean oil. Lecithin is a major component of mammalian cellular membranes giving lecithin-based liposomes a biomimetic or biological look-alike quality. Other ingredients which can be used to synthesize liposomes include, but are not limited to, naturally occurring and synthetic amphipathic lipids such as fatty acids, lysolipids, glucolipids, phospholipids with short chain fatty acids of 6–8 carbons in length, synthetic phospholipids, and others, see e.g. Huc et al. ("Huc") U.S. Pat. No. 5,244,672, Edgar et al. U.S. Pat. No. 5,498,420 and Unger et al. U.S. Pat. Nos. 5,469,854 and 5,580,575 the disclosures of which are hereby incorporated herein by reference thereto. These and other such materials are suitable liposome membrane forming materials for use in the practice of the invention, as will be understood by those skilled in the art.

Stabilizing agent. Some specific polymers useful as liposome stabilizing agents in practicing the invention are certain commercially available quaternized polysaccharides, especially celluloses, rich in quaternary groups, for example the CRODACEL Q (trademark) range of allyl quaternary cellulose polymers (Croda, Inc.), notably laurdimonium hydroxyethylcellulose, sold under the trademark CRODACEL QL, cocodimonium hydroxyethylcellulose, sold under the trademark CRODACEL QM and steardimonium hydroxyethylcellulose, sold under the trademark CRODACEL QS.

The CRODACEL Q (trademark) polymers belong to a class of polymers having repeating units of the following general structure:

wherein the backbone moiety can be a unit of a polycarbohydrate, a polysaccharide, a vinyl alcohol polymer, a copolymer of vinyl alcohol with vinyl acetate, or equivalent natural or synthetic polymers as known to those skilled in the art; R can be methylene, ethylene, or propylene; $R_1$–$R_4$ can be hydrogen or alkyl groups having from 1 to 20 carbon atoms, at least one of which is alkyl; where a is from 0 to 20; and $X^-$ is an anion, for example chloride or phosphate (equivalent).

In the CRODACEL Q (trademark) range of quaternized cellulose polymers, preferred in the practice of the invention for their suitability and commercial availability, the backbone moiety is an anhydroglucose unit; R is ethyl in each case, and one of $R_1$–$R_4$ is lauryl, cocoyl, stearyl or other medium chain alkyl group of about 10–20 carbon atoms; two of $R_1$–$R_4$ are methyl and $X^-$ is chloride. Other equivalent polymers usable as stabilizing agents in the practice of the invention can employ some or all of these substituents, as will be known or apparent to those skilled in the art. A medium chain allyl group, or equivalently hydrophobic group, for example as specified for one of $R_1$–$R_4$, is believed helpful in rendering the polymer compatible with the lipid component of the liposome structural material, typically lecithin, and in retaining the stabilizing polymer in the stabilizing liposome. Mixtures of one or more of the stabilizing agent polymers disclosed herein can also be used.

Where the stabilizing agent is a modified cellulose having the above formula, each anhydroglucose unit can have a maximum of three ethoxy substituents, as shown, but in practice, the average degree of ethoxy substitution will be substantially lower so that the indication of di-hydroxyethyl substitution should be regarded as a theoretical limit rather than a practical representation. Thus, each repeating anhydroglucose or saccharide unit contains up to two hydroxyethyl substituents and a quaternary ammonium group attached to the polysaccharide nucleus via a short polyethoxy chain. Polyquaternium 24 polymers, such as those available under the trademark QUATRISOFT LM-200 (Union Carbide Corporation), lack the longer alkyl group and the lipophilic character it confers, and are less preferred for the practice of the present invention.

Preferably the degree of substitution of the hydroxy alkylene group per backbone moiety is at least 1.0, and in the range of from 1.2 to 2.0. While substitution ratios as low as 0.2 or close to the theoretical limit of 2.0 may be useful, an average ratio of 0.5 moles to 1.5 moles of quaternary ammonium, or other cationic, groups per backbone moiety is preferred to provide adequate polarity and water solubility. In practice, a commercially available ratio of 1.2 moles of quaternary groups per glucose unit is useful, this being the approximate number for steardimonium hydroxyethylcellulose, a strong anion exchanger.

Some examples of further polymers that may be used include suitably modified or substituted polysaccharides other than cellulose, for example starch or chitosan; modified or substituted proteins, polypeptides of adequate molecular weight, or non-biological polymers (e.g. acrylates). Protein-based or biological polymers may bring allergenicity problems, depending upon their heterogenicity, and are accordingly not preferred for use in the practice of the invention. However, relatively homogenous polyamino acids, e.g. polylysine, have low immunogenicity and are more suitable for use as the backbone polymer for the stabilizing agents of the invention. Suitable substituents comprise quaternary amine groups for polarity and alkyl groups for lipophilicity.

Of particular importance is the quaternary nitrogen atom which provides a cationic binding site for anionic actives. The $R_4$ alkyl chain can provide a lipophilic anchor for lipid or lipophilic actives. the CRODACEL Q (trademark) range of quaternized celluloses are more fully described in a product data sheet entitled "Crodacel Q range" from Croda Chemicals Ltd., UK, the disclosure of which is hereby incorporated herein by reference thereto. They are supplied as somewhat hazy or opaque viscous concentrates intended for dilution and are known as film-forming agents with particular application in hair shampoos and conditioners, where their ability to be substantive to the hair, i.e. to attach themselves to the hair in a substantive manner, without creating build-up, is valuable. These and similar polymers suitable for use in the practice of this invention are well known in the literature and are described, for example, in U.S. Pat. No. 5,288,484 (Tashjian), U.S. Pat. No. 5,283,228 (Narayanan), U.S. Pat. No. 5,135,748 (Ziegler et al.) and U.S. Pat. No. 4,970,067 (Panandiker et al.), the disclosures of which are also hereby incorporated herein by reference thereto.

While the scope of the invention is limited only by what is defined in the appended claims, and equivalents thereof, and is neither limited by nor dependent upon the veracity of any particular theory, it is believed desirable for the stabilizing agent to have substantial cationic polarity and to be preferable for this polarity to be disposed on pendant groups that can locate themselves on or toward the outer surface of an individual liposome so as to coat the liposome with an aura of positive charge whereby neighboring liposomes tend to repel one another, or keep their distance one from another, and will have difficulty agglomerating. Other preferred structural characteristics of the stabilizing agents of the invention are an extended linear backbone and significant lipophilic groups enabling the polymeric stabilizing agent to enmesh lecithin or other liposome molecules and provide structural support tending to hold the individual liposome together. Accordingly, pursuant to this theory, preferred stabilizing agents of the invention should have sufficient cationic substitution, preferably, but not necessarily, quaternary ammonium, to provide such an external cationic coating or aura, but should not be so extensively cationically substituted that the polymer remains in solution throughout the preparation process. Nor should the cationic groups be mostly oriented towards the interior of the liposome where an entrapped aqueous or electrolytic medium may tend to attract such cationic groups. Preferably the stabilizing polymer should have sufficient lipophilic groups to anchor lipophilic portions of the liposome membrane forming compound.

Preferred embodiments of stabilizing agent polymers, notably the CRODACEL Q (trademark) range, have an average molecular weight of about 100,000 daltons, although a lower average molecular weight range, e.g down to 75,000 daltons, or even as low as 50,000 daltons can be used. There is no particular upper limit to the molecular weight of the restraining polymer, although it is contemplated that the average molecular weight will not exceed several million, e.g. 5 million daltons, but preferably does not exceed 1 million daltons. A preferred range for the average molecular weight is from 75,000 to 125,000 daltons.

Active agent. The stabilized liposome compositions of the invention can incorporate, and protect, a wide range of active agents, as is generally known to those skilled in the art. Preferred active agents include aqueous solutions or dispersions of cosmetic, dermatalogic or pharmaceutical active agents having topical, dermal, subdermal or systemic activity. A particularly preferred class of actives comprises relatively strong aqueous solutions of exfoliative alpha-hydroxy acids whose acidity is especially damaging to the stability of conventional liposome formulations. Aqueous alpha-hydroxy acid solutions having a concentration in excess of 10% by weight and up to about 25% by weight or more of acid, or mixed acids, can be well tolerated by the preferred liposome compositions of the invention.

Some active agents that may be incorporated in the liposomes of the invention comprise antioxidants including botanically derived polyphenols, for example procyanidin oligomers; free radical scavengers; topically active enzymes, for example, antibacterials, such as glucose oxidase, antioxidants such as superoxide dismutase, and proteolytic enzymes such as bromelain, (useful for enzyme peeling); other enzymes such as the DNA repair enzymes described above; exfoliative retinoids, such as retinol and retinol esters including retinol acetate, vitamin a palmitate; purified plant extracts and plant proteins; whitening agents such as arbutin; essential fatty acids, such as linoleic acid, linolenic acid and arachidonic acid; animal proteins, for example collagen, elastin and keratin; moisturizers, such as hyaluronic acid and other glycosaminoglycans; ultraviolet light filters; coated or uncoated organic pigments such as ultramarine blue; melanin or a sepia ink extract; other colorants or dyes, and perfumes.

A non-comprehensive catalog of therapeutic active agents, "drugs" appears in Unger '575, at col. 9, line 46 to col. 13, line 18. Except for any such agents that may require a gaseous ambience, such as that of the interior of Unger's liposomes, these therapeutics may also be used in the practice of the present invention.

Liposome preparation and size. The liposome compositions of the invention can be prepared by processing methods which are largely known to the art, save for the novel ingredients provided by the invention. Thus, typically, all ingredients are dissolved or dispersed in water or an aqueous solution with vigorous mixing at room temperature, and are then homogenized several times at high pressure to cause formation of liposomes. Liposomes produced by the methods of the invention are somewhat larger than some prior art liposomes, e.g. as taught by Edgar et al., and preferably have an average size in the range of about 75 to about 200 nm, preferably about 100 to 150 nm. If desired, the average size, or the size distribution, or both can be controlled by methods known to those s killed in the art for example as set forth in Unger '575 col. 14, line 49 to col. 15, line 5.

Cosmetic formulations. Cosmetic formulations, diluents or cosmetic vehicles are compositions applied externally to the skin, hair or nails for purposes of cleansing, beautifying, conditioning or protecting the body surface. Cosmetic formulations include but are not limited to water-in-oil or oil-in-water emulsions in cream or lotion form, sunscreens, toners, astringents, facial make-ups, powders, and skin cleansing compositions. The recipes for such compositions are well known to those skilled in the art and can be found in many publications in the field. A brief summary of some such cosmetic "diluents" that can be used in the practice of the invention appears in Wolf et al. U.S. Pat. No. 5,449,519, for example at column 4, line 25 to column 6, line 56, the disclosure of which is hereby incorporated herein by reference thereto. The stabilized liposome compositions of the invention are generally suitable for incorporation into such cosmetic compositions or "diluents" and the invention extends to the resultant liposome-containing compositions which have beneficial properties arising from the presence of the liposomes, for example new active ingredients, new concentrations of active ingredients, or simply better delivery of active ingredients with reduced loss of activity.

The stabilized liposomes of the invention can be used in such cosmetic compositions in any desired concentration or proportion that will provide an effective amount of active agent upon application, for example from 0.1 to 90 percent by weight of the total composition, preferably from 1 to 50 percent, and more preferably from 5 to 25 percent by weight of the total composition.

Some non-limiting examples of the practice of the invention will now be described by way of illustration.

EXAMPLE 1

Preparation of Liposomes Stabilized with a Quaternized Cellulose 8 g of highly purified hydrogenated soya lecithin (Phospholipon 90H, Nattermann—Germany) and 1 g of steardimonium hydroxypropyl cellulose (CRODACEL QS, Croda, Inc.) suspension (20% dry weight; Croda, Inc.) are added to 50 g distilled water and mixed vigorously at room temperature to obtain an homogeneous and highly viscous dispersion. Then 150 g distilled water is added and the resulting dispersion is homogenized several times at high pressure, using a High Pressure Homogenizer (Rannie—Denmark): 3 passes at 500 bars. The suspension is then diluted with water to a concentration in phospholipids of 20 g/L.

Control 1
Preparation of Pure Lecithin Liposomes
Following the procedure in Example 1, pure lecithin liposomes were prepared, as a control, by omitting the addition of the steardimonium hydroxypropyl cellulose.

Control 2
Preparation of Liposomes Stabilized with Stearylamine
8 g of highly purified hydrogenated soya lecithin (Phospholipon 90H; Nattermann—Germany) and 1 g of stearylamine (Croda, Inc.—Switzerland) are added to 50 g distilled water and mixed extensively at room temperature to obtain a homogeneous and highly viscous dispersion. Then 150 g distilled water is added and the resulting dispersion is homogenized several times at high pressure, using a High Pressure Homogenizer (Rannie—Denmark): 3 passes at 500 bars. The suspension is then diluted with water to a concentration in phospholipids of 20 g/L.

Control 3
Preparation of Commercially Available Liposomes
Liposomes are prepared using a commercially available preparation of non-hydrogenated lecithin dispersed in a hydrophilic medium (PRO-LIPO S, trademark, Lucas Meyer France S.A.) As described in the company's product data sheet, the lecithin (soya phosphatidylcholine) is pretreated to facilitate liposome formation and the preparation includes a small quantity of polar lipids. These are diluted as recommended by the supplier by the addition of water under mixing (750 rpm) at room temperature to obtain the final concentration in terms of phospholipid of 20 g/L.

Test A

Size Determinations Over Time

Size determination of the liposomes is conducted by a light scattering method employing a Coulter Nanosizer N4SD, after dilution of the suspension in a buffer, 50 nM sodium acetate, pH 5.6. Typical average sizes of such preparations range from 130 to 150 nanometers.

Size determinations were made on the four different liposomes compositions, each being at a concentration of 20 g/L. The suspensions are then mantained at 40° C. for 60 days and a second set of size determinations is performed. The results are shown in Table 1 below.

TABLE 1

Size Determinations

| Liposome type | Size on the first day | Size after 60 days | Comment |
| --- | --- | --- | --- |
| Example 1: Liposome stabilized with quaternized cellulose | 137 nm | 134 nm | stable |
| Control 1: Pure lecithin liposome | 123 nm | gelified | unstable |
| Control 2: Stearylamine-stabilized liposome | 111 nm | gelified | unstable |
| Control 3: Commercially available liposome | 222nm | 326 nm | some aggregation |

Only the quaternized cellulose-stabilized liposomes are stable under the test conditions. 40° C. is a high ambient temperature, about 104° F., which is above normal shelf storage temperatures, and is often used for accelerated stability tests for cosmetic formulations. A size increase of less than 20 percent after 60 days at 40° C. would indicate a sufficient stability to be valuable for some commercial purposes. The inventive composition of Example 1 was well within this limit, showing no significant size increase, whereas all the control compositions fell far short of such desired stability when examined by the described light-scattering test.

Test B

Temperature Stability

Liposomes stabilized with quaternized cellulose were compared with stearylamine stabilized liposomes at 80° C. for 4 hours. The aggregation rates of the liposomes were measured by determining the turbidity of the suspension by measuring the optical density ("OD")using orange light at 600 nm. A higher optical density denotes larger particles and an increase in optical density shows aggregation of liposomes. No optical density increase was noted for the liposomes stabilized with quaternized cellulose, even after 210 minutes. A 10% increase in optical density after 180 minutes would indicate commercially useful stability. The stearylamine stabilized liposomes showed an optical density increase of 50% after 90 minutes and the optical density multiplied by 4 after 3 hours.

Test C pH Stability

Quaternized cellulose liposomes were compared with commercially prepared liposomes at different pH levels. The pH level was adjusted by the addition of either hydrochloric acid or sodium hydroxide to the liposome suspensions and agitation during 5 minutes.

TABLE 2 pH Stability

| Liposome Type | pH = 11 | pH = 10 | pH = 6.5 | pH = 4.5 | pH = 2 |
| --- | --- | --- | --- | --- | --- |
| Control 3 Commercially Available | 205 nm | 210 nm | 235 nm | 450 nm | 480 nm |
| Example 1 Quaternized cellulose | 180 nm | 134 nm | 130 nm | 136 nm | 142 nm |

Surprisingly, the liposomes of Example 1 show excellent size stability at a strongly acidic pH 2, along with some agglomeration at an alkaline pH of 11. In contrast, the commercially available control 3 liposome preparation, more than doubled in size at pH 2.

Test D

Solvent and Surfactant Stability

Aliquots of solvent or surfactant were added to a quaternized cellulose liposome suspension until aggregation was detectable. The average sizes of the suspensions were measured after 10 minutes standing with the added solvent or surfactant.

Solvent: Increasing quantities of ethanol were added to a quaternized cellulose liposome suspension. The limit where the quaternized cellulose liposomes remained stable (i.e. there was no change in the average size of the liposome) was found to be 35% ethanol based on the water content of the liposome suspension.

Surfactants: Aliquots of an aqueous solution of a non-ionic surfactant (Hecameg) at a concentration of 13 g/L were added to a quaternized cellulose liposome suspension. The limit where the quaternized cellulose liposomes remained stable was found to be where the surfactant solution comprised 50% of the water in the liposome composition. The effect of a second surfactant was tested by adding increasing quantities of an aqueous solution of lauryl sulfate (an anionic surfactant) at a concentration of 13 g/L to a quaternized cellulose liposome suspension. The limit where the quaternized cellulose liposomes remained stable was also found to be where the lauryl sulfate solution comprised 50% of the water in the liposome composition.

The results of Tests B and D are summarized in Table 3 below.

TABLE 3

Temperature & Solvent/Surfactant Stability

| Liposome Preparation | TEST B 80° C. Stability OD Increase | TEST D Solvent/Surfactant Stability limit |
|---|---|---|
| Commercially useful limits | 10% at 180 min. | 20% ethanol 10% surfactant |
| Example 1: Quaternized cellulose | none at 210 min. | 35% ethanol 50% surfactant. |
| Control 2 | 50% at 90 min. | |
| Stearylamine | 300% at 180 min. | |

EXAMPLE 2
Stabilized Liposomes with Encapsulated Alpha-Hydroxy Acids 8 g of highly purified hydrogenated soya lecithin (Phospholipon 90H, Nattermann—Germany) and 1 g of steardimonium hydroxypropyl cellulose suspension (20% dry weight, Croda, Inc.) are added to 50 g distilled water and mixed extensively at room temperature to obtain a homogeneous and highly viscous dispersion. A solution of five commonly used alpha-hydroxy acids ("AHAs",Novarom—Germany) with the following concentrations of individual acids was used:

citric acid: 4% glycolic acid 20% malic acid: 1% salicylic acid 0.1% lactic acid: 25%.

16 g of this solution is slowly added to the above mixture and 100 g of distilled water is then added. The resulting dispersion is homogenized several times at high pressure using a high pressure homogenizer (Rannie—Denmark): 3 passes at 500 bars. The suspension is then diluted with water to a concentration based on phospholipids of 20 g/L. The resultant AHA concentraton in the lipsome product is 2% by weight. Encapsulation yield is measured by filtration of the suspension and assay of AHAs in the filtrate from which the filtered liposomes and encapsulated AHAs are removed. Encapsulation yield is above 70%. The pH of the composition is around 2.0.

Control 4
Commercial Liposomes with Encapsulated Alpha-Hydroxy Acids

As a control, the same alpha-hydroxy acid solution was encapsulated, using the commercially available liposome preparation referenced in Control 3, and using a similar procedure and proportions as Example 2. As reported by the manufacturer in the PRO-LIPO S (trademark) data sheet, up to 50% of the water solubles are encapsulated.

Test E
Aggregation Determinations

The liposome suspensions were stored at 4° C., and at room temperature, and their degree of aggregation was determined by light scattering. For commercial applications, it would be useful to have compositions showing no significant aggregation after 90 days. Known liposome preparations do not provide such stability, especially at the low pH levels provided by high concentrations of alphahydroxy acids.

Whether stored at room temperature or 4° C., the commercially available liposome suspensions aggregate rapidly and, after 15 days, the suspension is completely gellified. In contrast, the liposomes stabilized with quaternized cellulose, pursuant to the invention, showed no aggregation even after four months of storage at pH 2, a very low pH. The results of Test E are summarized in Table 4 below.

TABLE 4

Aggregation of AHA-containing Liposomes

| AHA-containing Liposome Preparation | Aggregation |
|---|---|
| Commercially useful limit | No aggregation after 90 days |
| Example 2: Quaternized cellulose stabilized | No aggregation after 120 days |
| Control 4: Commercial liposomes | Gellified after 15 days |

The foregoing tests show that the quaternized cellulose stabilized liposomes of Examples 1 and 2 have a remarkable stability to many of the parameters encountered in the formulation and distribution of cosmetic and pharmaceutical products, namely, temperature, pH, organic solvents such as ethanol, surfactants, long term storage and can even be loaded with very acidic aqueous concentrations of active agents, namely an AHA mixture, while remaining stable. Available tested known liposome preparations were markedly unstable by comparison and fell far short of the limits set forth herein for commercial usefulness.

In addition, as shown by comparing Example 2 with Control 4, the invention provides a method of preparing liposomes which by virtue of employing a cationically substituted and alkylated polymer as a stabilizing agent obtains a surprisingly high encapsulation of dissolved solids, in the case of Example 2, in excess of 70% by weight of AHAs are entrapped in the product lipsomes, as shown by a difference determination on the filtrate. The invention thus provides stabilized liposomes with excellent and enhanced solids loading as compared with the commercially available liposome preparation.

INDUSTRIAL APPLICABILITY

The present invention is particularly suitable for application in the cosmetic industry providing novel consumer cosmetic products, for example, creams, gels and lotions containing stabilized liposomes with encapsulated active ingredients, and the stabilized liposome compositions themselves.

While an illustrative embodiment of the invention has been described above, it is, of course, understood that various modifications will be apparent to those of ordinary still in the art. Such modifications are within the spirit and scope of the invention, which is limited and defined only by the appended claims.

We claim:

1. A method of encapsulating a high proportion of water soluble active agent in liposomes comprising mixing together:
    a) a liposome-forming structural material;
    b) an effective proportion of a quaternized polysaccharide stabilizing agent; and
    c) an effective proportion of a water-soluble active ingredient dissolved in sufficient of an aqueous medium to provide a dispersion medium for the liposomes;
and homogenizing the mixture to form liposomes wherein the quaternized polysaccharide agent is present in the liposomal membrane, providing support to the liposome-forming material to hold the liposome together and wherein the dissolved active ingredient is encapsulated in the liposomes.

2. A stabilized, aqueous dispersion of liposomes wherein the liposomes comprise, as structural components of individual liposomes:

a) an amphiphilic liposome-forming material; and b) a sufficient proportion of a quaternized polysaccharide stabilizing agent to stabilize the liposome dispersion against agglomeration;

wherein the quaternized polysaccharide agent is present in the liposomal membrane and provides support to the liposome-forming material to hold the liposome together.

3. A dispersion of liposomes according to claim 2 wherein the stabilizing agent comprises a quaternized cellulose having an average molecular weight of at least 50,000 daltons, the quaternary group having an alkyl substituent of from 10 to 20 carbon atoms.

4. A dispersion of liposomes according to claim 2 wherein the quaternized cellulose has a degree of substitution of quaternary ammonium groups per saccharide unit of at least 0.5.

5. A dispersion of liposomes according to claim 2 wherein the quaternized polysaccharide comprises laurdimonium hydroxyethylcellulose, cocodimonium hydroxyethylcellulose or steardimonium hydroxyethylcellulose.

6. A dispersion of liposomes according to claim 2 wherein the proportion of quaternized polysaccharide to liposomes is from about 0.01 to about 0.5 parts polysaccharide per part of liposome, by weight.

7. A dispersion of liposomes according to claim 2 wherein the proportion of quaternized polysaccharide to liposomes is from about 0.05 to about 0.2 parts polysaccharide per part of liposome, by weight.

8. A dispersion of liposomes according to claim 2 wherein the amphiphilic liposome-forming material comprises a liposome membrane-forming lecithin.

9. A dispersion of liposomes according to claim 2 wherein the liposomes comprise from about 0.5 to 10 percent by weight of the composition.

10. A dispersion of liposomes according to claim 2 wherein the individual liposomes contain an aqueous solution of a cosmetically or biologically active ingredient.

11. A dispersion of liposomes according to claim 10 wherein the active ingredient is acidic.

12. A dispersion of liposomes according to claim 2 wherein the quaternized polysaccharide comprises laurdimonium hydroxyethylcellulose, cocodimonium hydroxyethylcellulose or steardimonium hydroxyethylcellulose, the proportion of quaternized polysaccharide to liposomes is from about 0.01 to about 0.5 parts polysaccharide per part of liposome, by weight, wherein the amphiphilic liposome-forming material comprises a liposome membrane-forming amphiphilic lecithin in a proportion of from about 0.5 to 10 percent by weight of the composition and wherein the individual liposomes contain an aqueous solution of an acidic cosmetically or biologically active ingredient.

13. A dispersion of liposomes according to claim 2 having a stability such that they exhibit a size increase of less than 20 percent after 60 days at 40° C. and are substantially stable for at least 180 minutes at 80° C.

14. A dispersion of liposomes according to claim 2 being stable to an acidic pH of at least as low as 4.5.

15. A cosmetic or pharmaceutical composition comprising an effective amount of a liposome composition according to claim 2, said liposome composition comprising an effective amount of an active ingredient.

16. A dispersion of liposomes according to claim 2 comprising:

a) an aqueous medium;

b) liposomes dispersed in the aqueous medium; and c) sufficient of a water-soluble quaternized polymer stabilizing agent to stabilize the liposomes against agglomeration the polymer having repeating units of the following general structure:

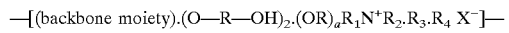

wherein the backbone moiety is a unit of a polycarbohydrate, a polysaccharide, a vinyl alcohol polymer, or a copolymer of vinyl alcohol with vinyl acetate; R is methylene, ethylene, or propylene; $R_1$–$R_4$ are hydrogen or alkyl groups having from 1 to 20 carbon atoms, at least one of which is alkyl; where a is from 0 to 20; and $X^-$ is an anion; wherein the degree of substitution of the hydroxy alkylene group per saccharide unit is at least 1.0; and the degree of substitution of the quaternary ammonium group per saccharide unit is at least about 0.5.

17. A dispersion of liposomes according to claim 2 wherein the liposome membrane forming compound has lipophilic portions and the stabilizing agent has sufficient lipophilic groups to anchor the lipophilic portions of the liposome membrane forming compound.

18. A dispersion of liposomes according to claim 2 exhibiting one or more of the following stability characteristics:

i) an optically determined size increase of less than about 20 percent after 60 days at about 40° C.;

ii) an optical density increase of not more than 10 percent after 180 minutes at 80° C.;

iii) size stability to agitation for five minutes at a pH of 4.5;

iv) size stability to 20 percent ethanol based upon the water content of the liposome dispersion; and v) size stability to 10 percent of a non-ionic surfactant based upon the water content of the liposome dispersion.

19. A dispersion of liposomes according to claim 2 having a stability providing an optical density increase of not more than 10 percent after 180 minutes at 80° C. and size stability to agitation for five minutes at a pH of 4.5.

20. A dispersion of liposomes according to claim 19 having size stability to agitation for five minutes at a pH of 2.

21. A dispersion of liposomes according to claim 20 wherein the liposome-forming material is a lecithin and the stabilizing agent is an acylated quaternized polysaccharide.

22. A dispersion of liposomes according to claim 2 wherein the stabilizing agent provides each individual liposome with an external positive charge whereby neighboring liposomes tend to repel one another.

23. A method according to claim 1 wherein the stabilizing agent comprises a quaternized cellulose having an average molecular weight of at least 50,000 daltons, the quaternary group having an alkyl substituent of from 10 to 20 carbon atoms.

24. A method according to claim 1 wherein the proportion of stabilizing agent to liposomes is from about 0.01 to about 0.5 parts polysaccharide per part of liposome, by weight.

25. A method according to claim 1 wherein an aqueous solution of a cosmetically or biologically active ingredient is entrapped within the liposome particles.

* * * * *